United States Patent
Becker et al.

(10) Patent No.: US 6,362,200 B1
(45) Date of Patent: Mar. 26, 2002

(54) ANTITUMOR DIBENZOFLUORENE DERIVATIVES

(75) Inventors: Frederick F. Becker, Houston; Bimal K. Banik, Missouri City, both of TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/634,102

(22) Filed: Aug. 8, 2000

Related U.S. Application Data (62) Division of application No. 09/203,650, filed on Dec. 1, 1998, now Pat. No. 6,184,224.

(51) Int. Cl.[7] ................ C07D 295/18; A61K 31/4453; A61K 31/495; A61P 35/00

(52) U.S. Cl. ...................... 514/319; 546/195

(58) Field of Search ................ 546/195; 514/319

(56) References Cited

FOREIGN PATENT DOCUMENTS

CA 743137 9/1966

OTHER PUBLICATIONS

Cherubim et al., "Synthesis and Biological Evaluation of Phenanthrene–Derived Carboxamides as Cytotoxic Agents," *Anti–Cancer Drug Design* 8:429–438 (1993).
Sami et al., "2–Substituted 1,2–Dihydro–3H–dibenz[de,h] isoquinoline–1,3–diones. A New Class of Antitumor Agent," *J. Med. Chem.* 36:765–770 (1993).
Yu et al., "Phenothiazines as Lipid Peroxidation Inhibitors and Cytoprotective Agents," *J. Med. Chem.* 35:716–724 (1992).
Leon et al., "Modulation of the Antitumor Activity by Methyl Substitutions in the Series of 7H–Pyridocarbazole Monomers and Dimers," *J. Med. Chem.* 30:2074–2080 (1997).
Bair et al., "2–[Arylmethyl)Amino]–2–Methyl–1,3–Propanediol DNA Intercalators. An Examination of the Effects of Aromatic Ring Variation on Antitumor Activity and DNA Binding," *J. Med. Chem.* 34:1983–1990 (1991).
Nakanishi et al., "Studies of Piperidine Derivatives," *J. Med. Chem.* 13:644–648 (1970).
"Chrysene," *Polycyclic Aromatic Hydrocarbon Structure Index*, No. 39, NIST Special Publication 922 (Aug. 18, 1998).
"7H–Benzo[hi]chrysene," *Polycyclic Aromatic Hydrocarbon Structure Index*, No. 106, NIST Special Publication 922 (Aug. 18, 1998).
"Dibenzo[c,l]chrysene," *Polycyclic Aromatic Hydrocarbon Structure Index*, No. 293, NIST Special Publication 922 (Aug. 18, 1998.
"Dibenzo[c,p]chrysene," *Polycyclic Aromatic Hydrocarbon Structure Index*, No. 276, NIST Special Publication 922 (Aug. 18, 1998).
"Dibenzo[def,mno]chrysene," *Polycyclic Aromatic Hydrocarbon Structure Index*, No. 121, NIST Special Publication 922 (Aug. 18, 1998).
Derwent Abstract, "Correlations Between Topological Resonance Energy of Methyl–Substituted benz[c]acridines, benzo[a]phenothiazines and chrysenes, and their carcinogenic or antitumor activities," Kurihara et al., Anticancer Res., 16(5A), p. 2757–65 (Sep.–Oct. 1996).

(List continued on next page.)

*Primary Examiner*—Richard L. Raymond
*Assistant Examiner*—Hong Kim
(74) *Attorney, Agent, or Firm*—Williams, Morgan and Amerson (57) ABSTRACT

Dibenzofluorene derivatives having a formula selected from the group consisting of

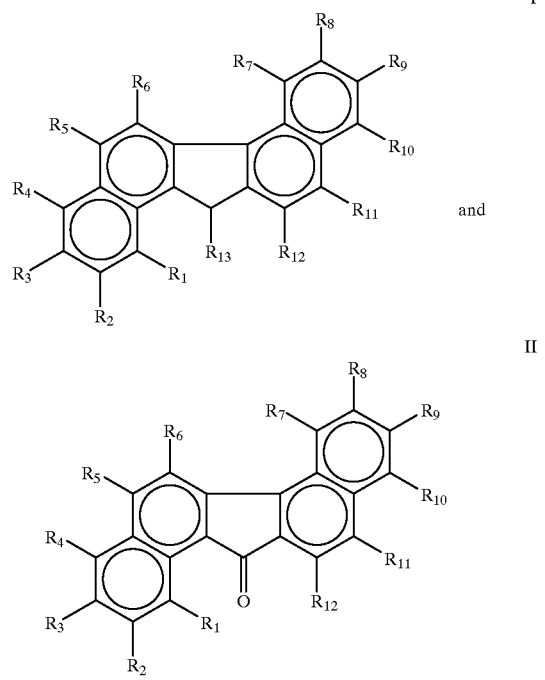

and salts thereof have antitumor activity. At least one of $R_1$–$R_{13}$ in formula (I) or $R_1$–$R_{12}$ in formula (II) is —$R_{14}Z$. $R_{14}$ is a substituted or unsubstituted amino or amido group having from 1–12 carbon atoms, and Z is a substituted or unsubstituted heterocyclic group having from 1–12 carbon atoms. The remainder of $R_1$–$R_{13}$ in formula (I) or $R_1$–$R_{12}$ in formula (II) are independently selected from the group consisting of hydrogen, hydroxyl, halogen, nitro, substituted or unsubstituted amino or amido groups having from 1–12 carbon atoms, and alkyl groups having 1–12 carbon atoms.

9 Claims, 3 Drawing Sheets

OTHER PUBLICATIONS

Derwent Abstract, "Use of Precision–Cut Liver Slices to Evaluate Species Differences in 2–Acetylaminofluorene–induced unscheduled DNA Synthesis," Lake et al., *Toxicol. Appl. Pharmacol.,* 138(2), p. 231–41 (Jun. 1996).

Derwent Abstract, "Absence of Mutagenicity of Benzo[c] Phenathridine Alkaloids in Somatic Cells of Drosophila Melanogaster: Comparison with 7,12–dimethylbenz[a] Anthracene and Chrysene," Perez–Chiesa et al., *Mutat. Res.,* 298(4), p. 277–83 (Feb. 1993).

Derwent Abstract, "Characterization of Cytochrome P–450 2B6 in Human Liver Microsomes," Mimura et al., *Drug Metab. Dispos.,* 21(6), p. 1048–56 (Nov.–Dec. 1993).

Derwent Abstract, "A Phase II Study of Crisnatol Mesylate in Patients with Ovarian Carcinoma," Smalley et al., *Invest. New Drugs,* 10(2), p. 107–12 (Jul. 1992).

Derwent Abstract, "Microbial Production of a Crisnatol Metabolite," Hufford et al., *Pharm. Res.,* 9(5), p. 623–5 (May 1992).

Derwent Abstract, "An Efficient Multiple–Exposure Analysis of the Toxicity of Crisnatol, a DNA Intercalator in Phase II Clinical Trials," Zucker et al., *Invest. New Drugs,* 10(1), pp. 1–15 (Apr. 1992).

Derwent Abstract, "New Anticancer Agents," Brown et al., *Cancer Chemother Biol. Response Modif.,* 12, p. 111–46 (1991).

Derwent Abstract, "Disposition, Metabolism, and Excretion of the Anticancer Agent Crisnaiol in the Rat," Patel et al., *Drug Metab. Dispos.,* 19(2), 491–7 (Mar.–Apr. 1991).

Derwent Abstract, "Metabolism of a Novel Antitumor Agent, Crisnatol, by a Human Hepatoma Cell Line, Hep G2, and Hepatic Microsomes. Characterization of Metabolites.," Patel et al., *Biochem. Pharmacol.,* 42(2), p. 337–46 (Jul. 5, 1991).

Derwent Abstract, "Phase I Evaluation of Crisnatol (BWA770U Mesylate) on a Monthly Extended Infusion Schedule," Cobb et al., *Sel. Cancer Ther.,* 7(2), pp. 85–91 (Summer 1991).

Derwent Abstract, "2–[Arylmethyl)Amino]–2–Methyl–1,3–Propanediol DNA Intercalators. An Examination of the Effects of Aromatic Ring Variation on Antitumor Activity and DNA Binding," Bair et al., *J. Med. Chem.,* 34(7), p. 1983–90 (Jul. 1991).

Derwent Abstract, "Crisnatol Mesylate: Phase I Dose Escalation by Extending Infusion Duration," Poplin et al., *Invest. New Drugs,* 9(1), p. 41–7 (Feb. 1991).

Derwent Abstract, "In Vitro Pharmacodynamic Assay for Cancer Drug Development: Application to Crisnatol, a New DNA Intercalator," Adams, *Cancer Res.,* 49(23), p. 6615–20 (Dec. 1, 1989).

Derwent Abstract, "Phase I and Clinical Pharmacology Trial of Crisnatol (BWA770U Mesylate) Using a Monthly Single–Dose Schedule," Harman et al., *Cancer Res.* 48(16), p. 4706–10 (Aug. 15, 1988).

Derwent Abstract, WO 9422773 (Oct. 13, 1994).

Derwent Abstract, RO 81292 (Feb. 28, 1983).

Derwent Abstract, RO 79546 (Jul. 30, 1982).

Derwent Abstract, RO 75308 (Feb. 17, 1982).

Derwent Abstract, JP 57020741 (Feb. 3, 1982).

Derwent Abstract, GB 873019.

Derwent Abstract, CA 743137.

Banik et al., "A Facile Reduction of Aromatic Nitro Compounds to Aromatic Amines by Samarium and Iodine," *Tetrahedron Letters* 39:7243–7246 (1998).

Banik et al., "Benzylic Oxidation by Sodium Bismuthate in Acetic Acid: A Simple Method for the Synthesis of Polycyclic Aromatic Ketones," *Tetrahedron Letters* 39:7247–7250 (1998).

"7H–Dibenzo[c,g]fluorene," *Polycyclic Aromatic Hydrocarbon Structure Index,* No. 85, NIST Special Publication 922 (Aug. 17, 1998).

"13H–Dibenzo[a,i]fluorene," *Polycyclic Aromatic Hydrocarbon Structure Index,* No. 92, NIST Special Publication 922 (Aug. 17, 1998).

"12H–Dibenzo[b,h]fluorene," *Polycyclic Aromatic Hydrocarbon Structure Index,* No. 96, NIST Special Publication 922 (Aug. 17, 1998).

"7H–Dibenzo[b,g]fluorene," *Polycyclic Aromatic Hydrocarbon Structure Index,* No. 88, NIST Special Publication 922 (Aug. 17, 1998).

"13H–Dibenzo[a,h]fluorene," *Polycyclic Aromatic Hydrocarbon Structure Index,* No. 97, NIST Special Publication 922 (Aug. 17, 1998).

"13H–Dibenzo[a,g]fluorene," *Polycyclic Aromatic Hydrocarbon Structure Index,* No. 90, NIST Special Publication 922 (Aug. 17, 1998).

Alumni–Bistocchi et al., *J. Heterocyclic Chem.* 17:993–995 (1980).

Groupe Europeen du Cancer du Sein, *Europ. J. Cancer* 3:75–77 (1967).

The value between parentheses indicates reaction times in hours

ANTITUMOR DIBENZOFLUORENE DERIVATIVES

This is a division of application Ser. No. 09/203,650, filed Dec. 1, 1998, now U.S. Pat. No. 6,184,224.

BACKGROUND OF THE INVENTION

The present invention relates to compounds having antitumor activity. The invention also relates to pharmaceutical compositions that contain one or more of those compounds, methods of using the compounds to inhibit tumor growth in mammals, and methods of preparing the compounds.

Many thousands of people are diagnosed with cancer each year, and although great advances have been made in cancer therapy, the existing treatments are not successful in many cases. Among the problems with existing therapies are (1) anticancer drugs administered to patients often have toxic effects on non-cancerous cells in the patient's body, (2) cancerous cells whose growth can be inhibited by certain drugs sometimes become resistant to those drugs, and (3) some cancers cannot be effectively treated with a single drug, and sometimes not even with a combination of different anticancer drugs. A long-standing need exists for new anticancer drugs that have one or more of the following characteristics: (1) ability to inhibit the growth of cancerous cells, (2) acceptable levels of toxicity to non-cancerous cells, (3) effectiveness against cancerous cells that are resistant to other drugs, and (4) a different mechanism of action than existing drugs, so that when the new drug is used in combination with an existing drug, the likelihood of the cancer cells developing cross-resistance is reduced.

SUMMARY OF THE INVENTION

The present invention concerns compounds having a formula selected from the group consisting of or salts thereof. In the above formulas, at least one of $R_1$–$R_{13}$ in formula (I) or at least one of $R_1$–$R_{12}$ in formula (II) is —$R_{14}$Z. $R_{14}$ is a substituted or unsubstituted amino or amido group preferably having from 1–12 carbon atoms. Z is a substituted or unsubstituted heterocyclic group preferably having from 1–12 carbon atoms. The remainder of $R_1$–$R_{13}$ in formula (I) or $R_1$–$R_{12}$ in formula (II) are independently selected from the group consisting of hydrogen, hydroxyl, halogen, nitro, substituted or unsubstituted amino or amido groups preferably having from 1–12 carbon atoms, and alkyl groups preferably having from 1–12 carbon atoms.

As mentioned above, salts of the compounds (I) and (II) are part of the present invention. Examples of suitable salts include but are not limited to the hydrochloride, iodide, and methane sulfonate salts.

In one embodiment of the invention where the compound has formula I, $R_{11}$ is —$R_{14}$Z, and $R_1$–$R_{10}$ and $R_{12}$–$R_{13}$ are independently hydrogen, hydroxyl, halogen, nitro, substituted or unsubstituted amino or amido having from 1–12 carbon atoms, or alkyl having 1–12 carbon atoms In another embodiment of the invention where the compound has formula II, $R_{11}$ is —$R_{14}$Z, and $R_1$–$R_{10}$ and $R_{12}$ are independently hydrogen, hydroxyl, halogen, nitro, substituted or unsubstituted amino or amido having from 1–12 carbon atoms, or alkyl having 1–12 carbon atoms.

$R_{14}$ preferably has the formula —$NHR_{15}$—, where $R_{15}$ is a substituted or unsubstituted aliphatic group having from 2–6 carbon atoms. $R_{15}$ preferably is selected from the group consisting of —$CO(CH_2)_nCO$—, —$(CH_2)_m$—, and —$CO(CH_2)_qCHCH(CH_2)_rCO$—, where n, m, q, and r are independently a number from 0–6. In one preferred embodiment of the invention, n is from 1–4, m is from 2–6, q is from 0–2, and r is from 0–2. Z preferably is selected from the group consisting of piperidinyl, piperazinyl, morpholinyl, thiomorpholinyl, pyrrolidinyl, hydroxyethyl piperazinyl, aminoethyl piperazinyl, and aminomethyldihydroxy piperidinyl.

Another aspect of the present invention is pharmaceutical compositions that comprise a compound as described above and a pharmaceutically acceptable carrier. Yet another aspect of the present invention is a method of inhibiting the growth of tumor cells, in which a tumor-inhibitory amount of a compound as described above is administered to a mammal.

Another aspect of the present invention is a method of synthesizing a cyclic hydrocarbon and keto compound. The method comprises the step of reacting a cyclic hydrocarbon compound that comprises at least two rings with a metal bismuthate in the presence of an acid. The metal bismuthate can be for example an alkali metal bismuthate such as sodium bismuthate. As another example, it can be zinc bismuthate. In certain embodiments of this method, the acid can be an organic acid such as acetic acid or a mineral acid such as sulfuric acid. Optionally the reaction can take place in the presence of an organic solvent, such as acetone. The cyclic hydrocarbon reactant preferably comprises from 10–50 carbon atoms.

The compounds and compositions of the present invention are useful in cancer therapy, either by themselves or in combination with other antitumor chemotherapy or radiation therapy.

DESCRIPTION OF SPECIFIC EMBODIMENTS

Polycyclic aromatic compounds are widely distributed in nature and are considered to be among the significant environmental carcinogens [1]. Previously, considerable research has been directed towards the synthesis of the polycyclic ring systems [2] and examination of their metabolic activation within target cells. Several hypotheses [3] have been proposed to establish the correlations between the structure of these metabolites, their cellular interactions and carcinogenicity. Eventually, most of the polycyclic metabolic products which act as carcinogens, intercalate with or bind covalently to DNA. Examination of several frequently used antitumor agents revealed two common structural features [4]: they have a planar ring system and a basic side chain. It could be predicted, therefore, that in addition to other cellular interactions these compounds would first demonstrate a strong interaction with the lipid domains of the plasma membranes and other membranes within the cell [5].

In some instances, antitumoral, DNA-intercalating drugs have been shown to interact with cell membranes and in some cases have demonstrated antitumor activities without further penetrating the cell structure. This then would put them in a class of drugs that have been called generically membrane stabilizing agents (MSA) [6]. These are agents which increase membrane stability against various stressors and often at higher concentration induce membrane destabilization. For example, they may act as anti-hemolytic agents at lower concentrations and cause hemolysis at higher concentrations. In order to determine the importance of these primary interactions with the plasma membrane of tumor cells in antitumor effects, we undertook an exploratory synthetic and biological evaluation of unique polycyclic aromatic compounds. This was based on our belief that the potential use of such compounds as antitumor agents has not been systematically explored [7], especially when specific modification is applied to enhance the membrane interaction as the primary effector of antitumor activity. On this basis, we began this systematic analysis by synthesizing a number of dibenzofluorene derivatives and studied their biological effects in vitro on a panel of human tumor cell lines.

A number of compounds of the present invention have been prepared, and are listed in Table 1.

TABLE 1

| Compound No. | Compound Name |
| --- | --- |
| Tx-37 | N-[11'-(13'H-Dibenzo[a,g]-fluorenyl)]-4-(4'N methyl-piperazinyl)-butane-1,4-dicarboxiamide |
| Tx-38 | N-[11'-(13'H-Dibenzo[a,g]-fluorenyl]-4-(1'-piperidinyl)-butane-1,4-dicarboxiamide |
| Tx-47 | N-[11'-(13'H-Dibenzo[a,g]-fluorenyl]-4-(4'N methyl-piperazinyl)-but-2-ene-1,4-dicarboxiamide |
| Tx-48 | N-[11'-13'H-Dibenzo[a,g]-fluorenyl]-4-(1'-piperidinyl)-but-2-ene-1,4-dicarboxiamide |
| Tx-49 | N-[11'-(13'H-Dibenzo[a,g]-fluorenyl))-4-(4'N methyl-piperazinyl hydrochloride)-butane-1,4-dicarboxiamide |
| Tx-50 | N-[11'-(13'H-Dibenzo[a,g]-fluorene-13'-one]-4-(4'N methyl-piperazinyl)-butane-1,4-dicarboxiamide |
| Tx-51 | N-[11'-(13'H-Dibenzo[a,g]-fluorene-13'-one]-4-(1'-piperidinyl)-butane-1,4-dicarboxiamide |
| Tx-66 | N-[11'-(13'H-Dibenzo[a,g]-fluorene-13'-hydroxy]-4-(4'N-methyl-piperazinyl)-butane-1,4-dicarboxiamide |
| Tx-67 | N-[11'-(13'H-Dibenzo[a,g]-fluorene-13'-hydroxy]-4-(1'-piperidinyl)-butane-1,4-dicarboxiamide |
| Tx-68 | N-[2'-(9'H-fluorenyl)]-4-(4'N methyl-piperazinyl)-butane-1,4-dicarboxiamide |
| Tx-69 | N-[2'-(9'H-fluorenyl))-4-(1'-piperidinyl)-butane-1,4-dicarboxiamide |

Methods for synthesizing the compounds of the present invention are described in the examples below. Therapeutic compositions containing these compounds will preferably also include one or more pharmaceutically acceptable carriers, such as saline solution, and may also include one or more pharmaceutically acceptable excipients and/or additional biologically active substances.

The compounds of the present invention can be used in methods of inhibiting the growth of tumor cells in mammals, particularly in humans. Specific human malignancies for which these compounds should be useful include breast, colon, ovarian, and prostate cancers, melanoma, leukemia/lymphomas, and possibly others as well. The compounds are administered to a mammal in an amount effective to inhibit the growth of tumor cells in the mammal. The administration can suitably be parenteral and by intravenous, intraarterial, intramuscular, intralymphatic, intraperitoneal, subcutaneous, intrapleural, or intrathecal injection. Such administration is preferably repeated on a timed schedule until tumor regression or disappearance has been achieved, and may be used in conjunction with other forms of tumor therapy such as surgery or chemotherapy with different agents. A compound of the present invention is preferably administered in a dose that is between approximately 0.01 and 100 mg/kg of body weight of the mammalian subject.

The present invention can be further understood from the following examples.

EXAMPLE 1

This example relates to synthesis of polycyclic aromatic ketones.

The oxidizing power of sodium bismuthate in acid media is proved by the facile conversion of bivalent manganese salts to heptavalent manganese. [8] In comparison to other, common oxidizing agents, the use of this reagent in synthetic organic chemistry has not been extensively explored. Rigby [9] demonstrated the cleavage of vicinal diols and the conversion of acyloins to α-diketones by sodium bismuthate. This reagent was also used for the oxidation of phenols [10], olefins [11] and α-ketols. [12] Recently, a few other bismuth derivatives were developed for the oxidation of various functional groups. [13]

Oxidation of benzylic methylenes to the ketones by DDQ [14], PCC [15], $CrO_3$ [16], tBuOOH [17], tetrapyridinesilver peroxydisulfate [18] is known in the literature. Recently, Harvey et al [19] reported a new oxidation method with n-BuLi in the presence of molecular oxygen. Although this method is attractive, it has several limitations. For example, oxidation of some structurally similar benzylic compounds could not be achieved by this method. Dimer formation in strong basic media was observed and mixtures of products were formed in some cases. Most importantly, extreme precaution has to be taken to get successful results as the method requires absolutely dry and inert media.

Figure 1:
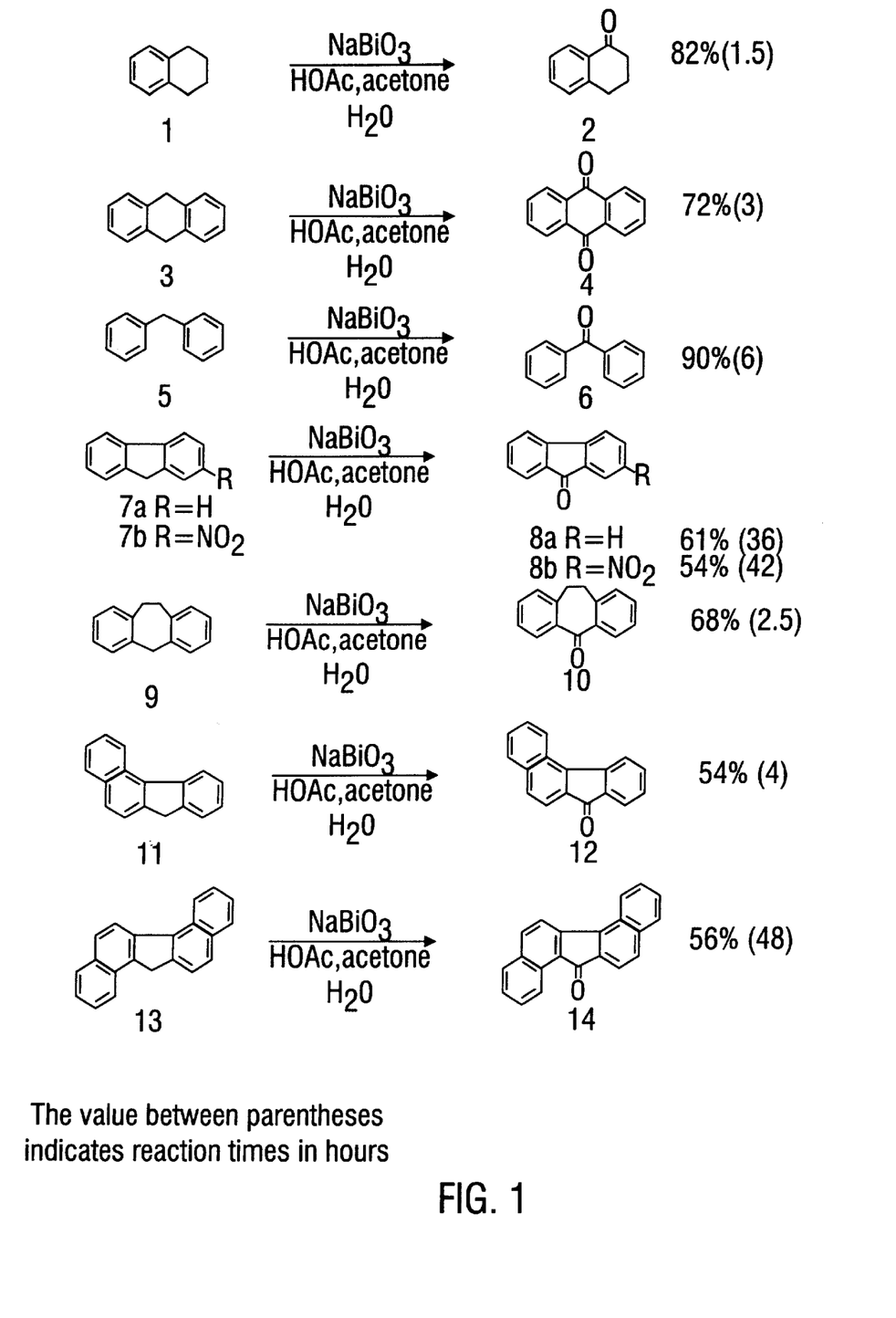
FIG. 1 depicts a synthesis scheme that is described in Example 1.

We have now oxidized benzylic methylenes to ketones under reflux condition, using sodium bismuthate in acetic acid. As shown in FIG. 1, commercially available tetralin (1), diphenylmethane (5), 9-10 dihydroanthracene (3), dibenzosuberane (9) fluorene (7a) and 2-nitrofluorene (7b) were readily converted to the respective ketones 2, 6, 4, 8a, 8b and 10 by sodium bismuthate in acetic acid. We selected two synthetic compounds, 2,3-benzo fluorene (11) and 13H-dibenzo[a,g] fluorene (13) reported by Harvey et al [14] for the oxidation study and produced the ketones 12 and 14 in good yield. The presence of acetic acid is required for the completion of the reaction. We found that the progress of the reaction became very slow when carried out without acetic acid. However, use of 10% sulfuric acid did not change the reaction time that was observed with acetic acid. In order to keep the reactants in contact with the oxidizing agent, acetone was added as a co-solvent.

Oxidation of 1, 5, 7, 9, 11 and 13 produced monoketones 2, 6, 8, 10, 12, and 14 in 50–90% yield. The presence of the diketone was not observed in the crude product while compound 3 produced a diketone 4 in 72% yield. No side products such as hydroxy, acetates, quinones or dicarboxylic acid were observed during this oxidation.

The mechanism of the sodium bismuthate induced oxidation is not firmly established. Oxidation of phenols by sodium bismuthate in neutral aromatic solvent has been shown to proceed by one-electron [10(e)] (through a radical intermediate) oxidation. Similar reaction in the presence of acetic acid as the solvent is believed to occur through a two-electron [10(f)] (carbonium ion) oxidation process. The suggested mechanism has a close similarity to the chromic acid [20] mediated benzylic oxidation. Thus, we hypothesize that our acid-catalyzed sodium bismuthate induced oxidation of benzylic methylenes may follow one of the processes mentioned above.

A representative procedure is as follows:

To the starting methylene compound (20 mmol) in acetic acid (4 mL, 50%) and acetone (2 mL), was added sodium bismuthate (80 mmol) and the mixture was heated to reflux under an argon atmosphere. At the end of reaction as indicated by TLC the mixture was filtered through a pad of celite and diluted with water (10 mL). The mixture was extracted with methylene chloride (3×20 mL). The combined organic layer was washed with sodium bicarbonate solution (3×10 mL, 10%), brine (10 mL), dried over anhydrous sodium sulfate and concentrated under reduced pressure. The resultant crude product was purified by column chromatography. All products have been characterized through a comparison of mp, TLC and NMR with authentic compounds.

EXAMPLE 2

This example concerns synthesis of dibenzofluorene derivatives.

Figure 2:
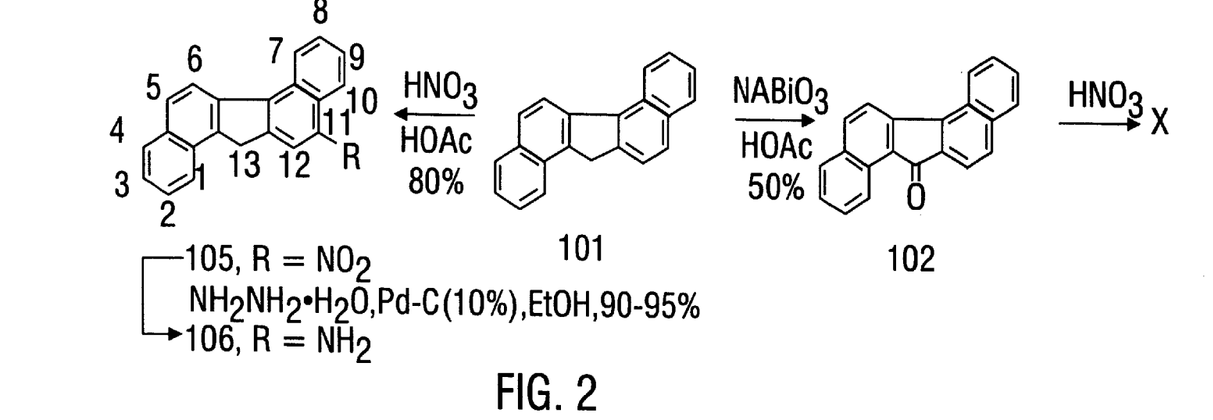
FIGS. 2–4 depict synthesis schemes that are described in Example 2.

We have developed a novel oxidation method for the conversion of benzylic methylenes to benzylic ketones in polycyclic systems by sodium bismuthate. Thus, as shown in FIG. 2, pentacyclic dibenzofluorene 101 was oxidized to the dibenzofluorenone 102 in good yield.

Figure 3:
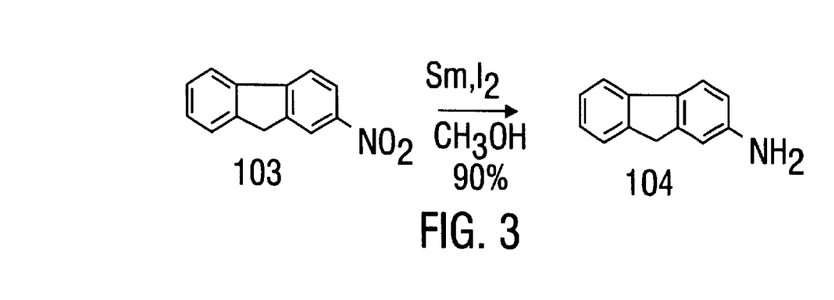

We have also shown a facile reduction of the polycyclic aromatic nitro compounds to polycyclic aromatic amines (for example, 3 to 4) by samarium metal in the presence of catalytic amounts of iodine (see FIG. 3).

Using these two methods, we became interested in examining the anti-tumor effects of structurally complex, angular dibenzofluorene [a,g] polycyclic systems with a very reactive bridged methylene group. We believe that a bridged unit in the polycyclic aromatic system could play an important role as this can form cation, anion and radical intermediates. This example describes the nitration study of the 13-H dibenzofluorene (101) and structure-activity relationship studies of several 13-unsubstituted and 13-substituted diamides (110, 111 and 112).

We prepared pentacyclic dibenzo[a,g] fluorene (110) in 20% yield by following the method reported by Harvey [21]. Functionalization of benzene and naphthalene derivatives by electrophilic reaction [22] is routine organic chemistry. The orientation of the electrophile in such monocyclic or bicyclic derivatives is predictable. Similar substitution reaction in polycyclic aromatic system is extremely difficult and the site of attack does not follow any known orientation rule. In fact, very little is known about the electrophilic substitution reaction in polycyclic aromatic system [23].

We planned to link a 4-carbon chain side chain with a heterocyclic base at the end to the aromatic ring through nitrogen [24]. Therefore, our task was to prepare amino dibenzofluorene 106 for the subsequent derivatization. Towards this goal, we reacted the ketone 102 with nitric acid in acetic acid under different conditions and failed to get any desired nitro derivative. However, the hydrocarbon 101 produced a single nitro compound 105 with nitric acid-acetic acid at 0–5° C. in 80% yield. (See FIG. 2.) The location of the nitro group in the aromatic system was determined by nmr spectra. The nmr spectrum (400 MHz) of the known hydrocarbon 101 was taken. Based on the homonuclear decoupling and COSY nmr studies, all the protons in 101 were assigned as follows: (400 MHz, CDCl$_3$)δ:8.81 (d, 1H, J=8.46 Hz, H$_7$), 8.50 (d, 1H, J=8.68 Hz, H$_6$), 8.02 (d, J=8.22 Hz, H$_1$), 7.89–7.96 (m, 3H, H$_4$, H$_5$, H$_{10}$), 7.70 and 7.79 (2H, ABq, J=8.23 Hz, H$_{11}$, H$_{12}$), 7.60–7.65 (m, 1H, H$_8$), 7.45–7.54 (m, 3H, H$_2$, H$_3$, H$_9$). These assignments were supported by the data reported by Jones et al [25]. The nmr spectrum of the nitro compound 105 revealed the absence of the AB quartet which was present in 101. The spectrum of 105 showed a new singlet at δ8.39 and a new doublet at δ8.44 (J=8.75 Hz). We eliminated positions C$_1$, C$_4$, C$_7$ and C$_{10}$ for the nitro group because of the singlet at δ8.44. The positions C$_5$, C$_6$, C$_8$ and C$_9$ were eliminated based on the homonuclear decoupling and COSY experiment. The region (δ7.5–7.6) of the hydrocarbon 101 remained unaffected in 105 clearly ruled out positions C$_2$ and C$_3$ for the nitro group in 105. We eliminated position C$_{12}$ because of the downfield doublet at δ8.44. The $^{13}$C nmr spectrum of 105 showed the presence of nine quaternary carbons. The signal at δ123.58 due to the C$_{11}$ carbon (verified by HETCOR study) was not present in the spectrum of 105. A new peak at δ145.24 appeared because of the nitro group. Thus, we assigned C$_{11}$ as the site of the nitro group in 105 based on extensive nmr study.

Reduction of the nitro compound 105 to the amino compound 106 was carried out by Pd-C (10%)-ammonium formate [26], samarium-iodine and Pd-C (10%)-hydrazine hydrate [27]. We found hydrazine hydrate and Pd/C (10%) gave the best results.

Our next task was to prepare the side chains 109 and to couple them to the amine 106. (See FIG. 4.) The acid 108 was prepared by refluxing succinic anhydride (107) with piperidine (108a) and N-methylpiperazine (108b). The amine 106 was then condensed with the side chains 109 by mixed anhydride method. [28]

The desired diamides 110 were isolated by column chromatography. The benzylic methylene group in 110 was oxidized by molecular oxygen [29] to get the ketone 111 which was subsequently reduced to the alcohol 112. All new compounds gave satisfactory spectral data.

Figure 4:
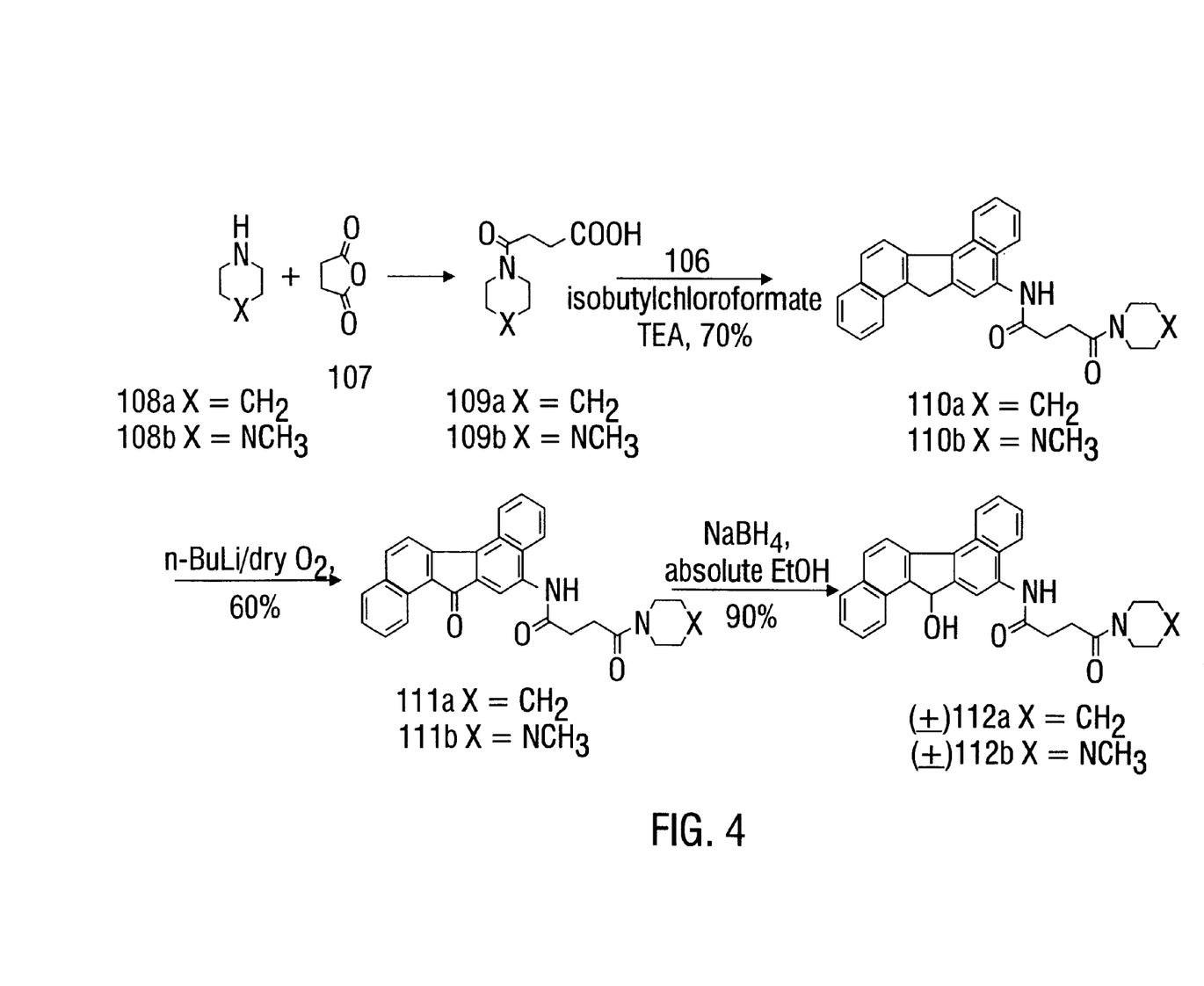

The compounds of this example (see FIGS. 2, 3, and 4) correlate to the listing of compounds by Tx number in Table 1 as follows:

| Compound | Compound Tx No. |
| --- | --- |
| 110a | Tx-38 |
| 110b | Tx-37 |
| 111a | Tx-51 |

-continued

| Compound | Compound Tx No. |
|---|---|
| 111b | Tx-50 |
| 112a | Tx-67 |
| 112b | Tx-66 |

EXAMPLE 3

Dibenzofluorene In Vitro Cytotoxicity Testing

Every dibenzofluorene derivative was tested, as will be described below, against six to eight cultured, tumor cell lines of human and/or animal origin, at least half of which were selected from the NCI panel of test tumors. In each experiment, Adriamycin (ADR) was used as a maximally positive control. Subsequent to our determination that the dibenzofluorene derivative Tx-37 demonstrated consistent, highly positive effects, it was also included in the panel of test agents in every experiment where dibenzofluorene derivatives were tested.

In Vitro Cytotoxicity Determinations

Data are $IC_{50}$ values (MTT assay) reported as µg/ml for 72 hours continuous exposure to the drug. Drugs were prepared in DMSO:PEG300 (1:1). Further, dilutions were made in a cell culture medium with fetal bovine serum.

| Test Tumor Lines | |
|---|---|
| BRO | human melanoma |
| HT-29 | human colon adenocarcinoma |
| P388/0 | murine lymphatic leukemia |
| MCF-7 | human breast carcinoma |
| HL-60 | human promyelocytic leukemia |
| OVCAR 3 | human ovarian carcinoma |

Additional tumor lines against which the drugs were tested in certain series included L1210 (leukemia), PC3 (prostate) and several others.

Compounds were evaluated for solubility characteristics in vehicles which would be appropriate for use in cell culture. The compounds were added to the cell lines under continuous culture for 72 hours. Inhibition of growth relative to control cell culture was determined by the MTT method at the end of 72 hours. This is a test of the relative ability of a compound to inhibit cell growth not survival. However, inhibition of growth may reflect cell death and/or cytostasis.

Summarized results of the in vitro cytotoxicity testing, specifically average $IC_{50}$ values for the various tumor lines, are given in Table 2.

TABLE 2

| Agent | # Runs | P388/0 | BRO | HT-29 | MCF-7 | OVCAR-3 | HL-60 |
|---|---|---|---|---|---|---|---|
| Tx-37 | 5 | 2.0 | 1.8 | 1.9 | 3.0 | 1.9 | 1.6 |
| Tx-38 | 3 | 42.9 | 46.4 | 34.4 | 22.8 | 39.5 | 14.9 |
| Tx-47 | 1 | 15.4 | 1.2 | 16.7 | 20.2 | 1.1 | 1.2 |
| Tx-48 | 1 | 71.5 | 22.6 | 52.2 | 18.3 | 23.4 | 30.1 |
| Tx-49 | 1 | 3.1 | 2.5 | 2.5 | 5.7 | 2.8 | 2.5 |
| Tx-50 | 2 | 3.7 | 11.2 | 10.0 | 18.1 | 6.6 | 4.0 |
| Tx-51 | 1 | 55.4 | 47.2 | 65.1 | 27.0 | 16.2 | 32.0 |
| Tx-66 | 1 | 2.1 | 6.0 | | 5.9 | 4.2 | 2.0 |
| Tx-67 | 1 | 9.2 | 14.7 | | 8.9 | 8.8 | 5.6 |
| Tx-68 | 1 | 41.7 | | | 18.2 | 31.7 | |
| Tx-69 | 1 | 41.5 | | | 28.9 | 52.6 | |

An $IC_{50}$ value above 50 µg/ml indicates that there was insufficient cytotoxicity of the compound to achieve a 50% inhibition of cell growth at 50 µg/ml. In some cases, we observed cytotoxicity at 100 µg/ml but few of the drugs are readily soluble at this concentration and the data are not reliable.

ADR invariably produced the described anti-tumor effect against all tumor lines at concentrations lower than 1 µg/ml of culture media. The effect of the Tx- compounds was divided into five activity groups as described below. In all cases, if activity against a single tumor line differed radically from that against all others, notation was made of this specificity but the agent was grouped as determined by the majority of the results.

Group A. These agents were effective against all tumor lines at concentrations under 5 µg/ml. Some of these compounds were effective at less than 1 log difference from the activity of ADR.

Group B. These agents were effective against all tumor lines at less than 10 µg/ml.

Group C. These agents were effective against one-third to one-half of all tumor lines tested at levels less than 10 µg/ml.

Group D. These agents were effective against one or two of the six to eight tumor lines tested at concentrations of less than 10 µg/ml.

Group E. These agents produced some anti-tumor effect at doses above 10 µg/ml but less than 20 µg/ml.

Group F. These agents were "effective" against some tumor lines above 20 µg/ml but often demonstrated no anti-tumor effect.

TABLE 3

| GROUP A |
|---|
| Tx-37 |
| Tx-49 |
| Tx-66 |
| GROUP B |
| Tx-50 |
| Tx-67 |
| GROUP C |
| Tx-47 |
| GROUP E |
| Tx-68 |
| GROUP F |
| Tx-38 |
| Tx-48 |
| Tx-51 |
| Tx-69 |

In summary of these findings, the most active compound produced in this series was Tx-37, the dibenzofluorene molecule with a terminal N-methyl piperazine heterocyclic ring. While the hydrochloride salt (Tx-49) or the addition of a hydroxyl moiety at position 13 (Tx-66), produced minor change in the activity, the substitution of a ketone moiety at position 13 (Tx-50) produced a slight diminution in activity. The insertion of an unsaturated bond in the alkyl chain at Tx-37 (Tx-47) reduced its activity significantly. Tx-38 with a terminal piperidine heterocyclic ring demonstrated no significant anti-tumor activity and the insertion of an unsaturated bond in this molecule produced little or no change (Tx-48). However, the addition of the hydroxyl moiety at position 13, which caused minor change in Tx-37, greatly increased the activity of Tx-38 (Tx-67). As we have reported in other compounds based on other polycyclic ring structures, those that terminate in a N-methyl piperazine ring again demonstrated far greater activity than those that terminated in a piperidine ring. Thus, Tx-38 and Tx-51 possess little or no activity when compared with the significant activities of Tx-37 and Tx-50 against all tumor lines. Modification of other components of the molecule, however, such as insertion of the hydroxyl moiety at position 13 of Tx-38 (Tx-67) often reduced or eliminated these differences; in this case by greatly enhancing its activity.

The preceding description of specific embodiments of the present invention is not intended to be a complete list of every possible embodiment of the invention. Persons skilled in this field will recognize that modifications can be made to the specific embodiments described here that would be within the scope of the present invention.

REFERENCES

The following references, to the extent that they provide exemplary procedural or other details supplementary to those set forth herein, are specifically incorporated herein by reference.

[1] For a general review see: Freudenthal R, Jones P W. Carcinogenesis—a comprehensive survey. New York: Raven Press, 1976; vol.1–3.

[2] For a recent example see: Harvey R G. Polycyclic aromatic hydrocarbons. Wiley-VCH, 1997.

[3] Di Raddo P, Chan T H. J. Org. Chem. 1982;47:1427 and references cited therein.

[4] For some recent examples: (a) Cherubim P, Deady L W, Dorkos M, Quazi N H, Baguley B C, Denny W A. Anti-cancer drug design. 1993;8:429. (b) Palmer B D, Lee H H, Baguley B C, Denny W A. J. Med. Chem. 1992;35:258. (c) Atwell G J, Rewcastle G W, Baguley B C, Denny W A. J. Med. Chem. 1987;30:664 and references cited therein.

[5] Wingard L B, Tritton T R. Cancer Res. 1985;45:3529.

[6] (a) Jorgensen K, Ipsen J H. Biochem. Biophys. Acta. 1991;1062:227. (b) Kanaho Y, Sato T. Mol. Pharm. 1981; 20:704.

[7] Bair K W, Tuttle R L, Knick V C, Cory M, McKee D D. J. Med. Chem. 1990;33:2385.

[8] (a) Burstein, G. T.; Wright, G. A. *Nature* (London), 1969, 221, 169. (b) Vogel, A. I. Qualitative Inorganic Analysis, Longman Scientific and Technical: England; Wiley: New York, 1987.

[9] Rigby, W. *J Chem. Soc.* 1950, 1907; 1951, 793.

[10] (a) Hewgill, F. R.; Kennedy, B. R.; Kilpin, D. *J. Chem. Soc.* 1965, 2904. (b) Hewgill, F. R.; Middleton, B. S. *J. Chem. Soc.* 1965, 2914. (c) Adderly, C. J. R.; Hewgill, F. R. *J. Chem. Soc. C.* 1968, 2770. (d) Adler, E.; Holmberg, K.; Ryrfor, L. O. *Acta Chem. Scand. Ser. B*, 1974, 28, 888. (e)Kon, E.; McNelis, E. *J. Org Chem.* 1975, 40, 1515. (f) Kon, E., McNelis, E. *J. Org. Chem.* 1975, 41,1646.

[11] Truesdale, L. K.; Reuman, M. E. *J. Org. Chem.* 1980, 45, 726.

[12] Floresca, R.; Kurihara, M.; Watt, D.; Demir, A. *J. Org. Chem.* 1993, 58, 2196.

[13] (a) Barton, D. H. R.; Finet, J. P. *Pure AppL Chem.* 1987, 59, 937. (b) Abramovitch, R. A.; Barton, D. H. R.; Finet, J. P. *Tetrahedron*, 1988, 44, 3039. (c) Finet, J. P. *Chem. Rev.* 1989, 89. (d) Firouzabadi, H.; Mohammadpour-Baltork, I. *Bull. Chem. Soc. Jpn.* 1992, 65, 1131. (e) Postel, M. Dunach, E. *Coordination Chemistry Rev.* 1996, 155, 127.

[14] Lee, H.; Harvey, R. G. *J. Org. Chem.* 1988, 53, 4587.

[15] (a) Rathore, R.; Saxena, N.; Chandrasekaran, S. *Synth. Commun.* 1986, 16, 1493. (b) Maurer, J. L.; Berchier, F.;Serino, A. J.; Knobler, C. B.; Hawthrone, M. F. *J. Org. Chem.* 1990, 55, 838. (c) Ghosh, S.; Banik, B. K.; Ghatak, U. R. *J. Chem. Soc., Perkin Trans*, 1991, 3195. (d) Ghosh, A. K.; Ray, C.; Ghatak, U. R. *Tetrahedron Lett*. 1992, 33, 655. (e) Ghosh. A. K., Mukhopadhyay; Ghatak, U. R. *J Chem. Soc., Perkin Transl* 1994, 327.

[16] (a) Wenkert, E.; Jackson, B. G. *J. Am. Chem. Soc.* 1958, 211. (b) Ghatak, U. R.; Chattediee, N. R.; Banedjee, A. K.; Chakravarty, J.; Moore, R. E. *J. Org. Chem.* 1969, 34, 3739. (c) Banik, B. K.; Ghosh, S.; Ghatak, U. R. *Tetrahedron*, 1988, 44, 6947.(d) Banik, B. K.; Ghatak, U. R. *Synth. Commun.* 1989, 19, 1351.

[17] Muzart, J. *Tetrahedron Lett*. 1987, 28, 2131.

[18] Firouzabadi, H.; Salechi, P.; Sardarian, A. R.; Seddighi, M. *Synth. Commun.* 1991, 21, 1121.

[19] Harvey, R. G.; Abu-shqara, E.; Yang, C. *J. Org. Chem.* 1992, 57, 6313.

[20] (a) Wiberg, K. B.; Evans, R. J. *Tetrahedron*, 1960, 8, 313. (b) Rocek, J. *Tetrahedron Lett*. 1962, 4, 135.

[21] Harvey, R. G.; Pataki, J.; Cortez, C.; DiRaddo, P.; Yang, C. *J. Org. Chem.* 1991, 56, 1210.

[22] Ranu, B. C.; Ghosh, K. Jana, U. *J. Org Chem.* 1996, 61, 9546 and references cited therein.

[23] Minabe, M.; Cho, B. P.; Harvey, R. V. *J. Am. Chem. Soc.* 1989, 111, 3809.

[24] Palmer, B. D.; Lee, H. H; Baguley, B. C., Denny, W. A. *J. Med. Chem.* 1992, 35, 258.

[25] Jones, D. W.; Matthews, R. S.; Bartle, K. D. *Spectrochim Acta, Part A*, 1972, 28, 2053.

[26] Bose, A. K.; Banik, B. K.; Barakat, K. J.; Manhas, M. S. *Synlett*, 1993, 575.

[27] Moore, R. E.; Furst, A. *J. Org. Chem.* 1958, 23, 1504.

[28] Holzapfel, C. W.; Pettit, G. R. *J. Org. Chem.* 1985, 50, 2323.

[29] Harvey, R. G.; Abu-Shqara, E.; Yang, C. X *J. Org. Chem.* 1992, 57, 6313.

What is claimed is:

1. A compound having a formula selected from the group consisting of

11 and or a salt thereof;

where $R_{11}$ is —$R_{14}Z$, where $R_{14}$ has the formula —$NHR_{15}$—, where $R_{15}$ is selected from the group consisting of —$CO(CH_2)_nCO$—, —$(CH_2)_m$—, and —$CO(CH_2)_qCHCH(CH_2)_rCO$—, where n is from 1–4, m is from 2–6, q is from 0–2 and r is from 0–2, and Z is a substituted or unsubstituted piperidinyl group having from 5–12 carbon atoms;

where $R_1$–$R_{10}$, $R_{12}$, and $R_{13}$ are independently selected from the group consisting of hydrogen, hydroxyl, halogen, nitro, amino, amido, and alkyl groups having 1–12 carbon atoms.

2. The compound of claim 1, where Z is selected from the group consisting of piperidinyl and aminomethyldihydroxy piperidinyl.

3. The compound of claim 1, where the compound is:
N-[11'-(13'H-Dibenzo[a,g]-fluorene-13'-hydroxy)]-4-(1'-piperidinyl)-butane-1,4-dicarboxiamide.

4. A pharmaceutical composition, comprising:
(a) a compound having a formula selected from the group consisting of and

12

-continued or a salt thereof;

where $R_{11}$ is —$R_{14}Z$, where $R_{14}$ has the formula —$NHR_{15}$—, where $R_{15}$ is selected from the group consisting of —$CO(CH_2)_nCO$—, —$(CH_2)_m$—, and —$CO(CH_2)_qCHCH(CH_2)_rCO$—, where n is from 1–4, m is from 2–6, q is from 0–2 and r is from 0–2, and Z is a substituted or unsubstituted piperidinyl group having from 5–12 carbon atoms;

where $R_1$–$R_{10}$, $R_{12}$, and $R_{13}$ are independently selected from the group consisting of hydrogen, hydroxyl, halogen, nitro, amino, amido, and alkyl groups having 1–12 carbon atoms; and (b) a pharmaceutically acceptable carrier.

5. The composition of claim 4, where Z is selected from the group consisting of piperidinyl and aminomethyldihydroxy piperidinyl.

6. The composition of claim 4, where the compound is:
N-[11'-(13'H-Dibenzo[a,g]-fluorene-13'-hydroxy)]-4-(1'-piperidinyl)-butane-1,4-dicarboxiamide.

7. A method of inhibiting the growth of tumor cells, comprising the step of administering to a mammal an amount effective to inhibit tumor cell growth of a compound having a formula selected from the group consisting of and -continued

II or a salt thereof;

where $R_{11}$ is —$R_{14}Z$, where $R_{14}$ has the formula —$NHR_{15}$—, where $R_{15}$ is selected from the group consisting of —$CO(CH_2)_nCO$—, —$(CH_2)_m$—, and —$CO(CH_2)_qCHCH(CH_2)_rCO$—, where n is from 1–4, m is from 2–6, q is from 0–2 and r is from 0–2, and Z is a substituted or unsubstituted piperidinyl group having from 5–12 carbon atoms;

where $R_1$–$R_{10}$, $R_{12}$, and $R_{13}$ are independently selected from the group consisting of hydrogen, hydroxyl, halogen, nitro, amino, amido, and alkyl groups having 1–12 carbon atoms.

8. The method of claim 7, where Z is selected from the group consisting of piperidinyl and aminomethyldihydroxy piperidinyl.

9. The method of claim 7, where the compound is:
N-[11'-(13'H-Dibenzo[a,g]-fluorene-13'-hydroxy)]-4-(1'-piperidinyl)-butane-1,4-dicarboxiamide.

* * * * *